United States Patent [19]

Demus et al.

[11] Patent Number: 4,668,426

[45] Date of Patent: May 26, 1987

[54] LIQUID CRYSTALLINE SUBSTANCES

[75] Inventors: Dietrich Demus; Horst Zaschke, both of Halle; Reinhard Paschke, Halle-Neustadt; Adalbert Wiegeleben, Zörbig, all of German Democratic Rep.

[73] Assignee: VEB Werk für Fernsehelektronik im VEB Kombinat Mikroelektronik, Berlin, Fed. Rep. of Germany

[21] Appl. No.: 717,419

[22] Filed: Mar. 29, 1985

[30] Foreign Application Priority Data

Apr. 9, 1984 [DD] German Democratic Rep. ... 617772

[51] Int. Cl.$^4$ .................... C09K 19/34; G02F 1/13; C07D 401/02; C07D 213/79
[52] U.S. Cl. ..................... 252/299.61; 546/326; 544/333; 350/350 R; 252/299.5
[58] Field of Search .............. 252/299.61, 299.64, 252/299.63, 299.66; 546/326; 544/333; 350/350 R

[56] References Cited

U.S. PATENT DOCUMENTS

| | | | |
|---|---|---|---|
| 3,915,883 | 10/1975 | Van Meter et al. | 252/299 |
| 4,001,137 | 1/1977 | Steinstrasser | 252/299.67 |

FOREIGN PATENT DOCUMENTS

| | | | |
|---|---|---|---|
| 56501 | 7/1982 | European Pat. Off. | 252/299.61 |
| 164721 | 12/1985 | European Pat. Off. | 252/299.61 |
| 85/109569 | 6/1985 | Japan | 252/299.61 |
| 85/149564 | 8/1985 | Japan | 252/299.61 |
| 86/68467 | 4/1986 | Japan | 252/299.61 |
| 8200654 | 3/1982 | World Int. Prop. O. | 252/299.5 |
| 2092169 | 8/1982 | United Kingdom | 252/299.61 |

OTHER PUBLICATIONS

Green et al., IBM Technical Disclosure Bulletin, vol. 15, No. 8, pp. 2467–2468, (Jan. 1973).
Dewar et al., Liq. Cryst. Ord. Fluids, vol. 2, pp. 733–741.
Pavluchenko et al., J. de Physique, Apr. 1979, pp. C1–4.
Karamyshea et al., MCLC, 1981, vol. 67, pp. 241–252.
Nash et al., MCLC, 1974, vol. 25, pp. 299–321.
Pavluchenko et al., MCLC, 1976, vol. 37, pp. 35–46.
Schubert, Wiss. Z. Univ. Halle, 1970, pp. 1–18.
Dewar et al., J. Amer. Chem. Soc., 97:23, Nov. 1975, pp. 6658–6666.

*Primary Examiner*—Teddy S. Gron
*Assistant Examiner*—J. E. Thomas
*Attorney, Agent, or Firm*—Jordan and Hamburg

[57] ABSTRACT

Nematic liquid crystalline substances as additives in mixtures for electro-optical systems for the rendition of numbers, symbols and images. The additives provide new liquid crystalline substances of broad mesophase ranges which improve the chemical stability of the substance mixtures. It has been found that liquid crystalline 5-alkyl-pyridine-2-carboxylic acid esters of the general formula

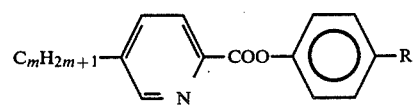

wherein R =

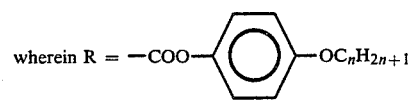

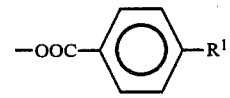

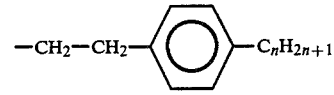

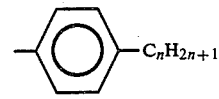

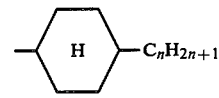

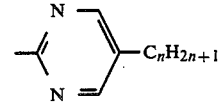

$R^1 = -OC_nH_{2n+1}$, CN, $-C_nH_{2n+1}$ wherein m, n = 1 to 8 are suitable for utilization in mixtures for electro-optical displays for the rendition of numbers, symbols and images.

17 Claims, No Drawings

LIQUID CRYSTALLINE SUBSTANCES

BACKGROUND OF THE INVENTION AND PRIOR ART STATEMENT

The invention relates to nematic liquid crystalline substances as additives in mixtures for electro-optical systems, which by utilizing the possibility of changing optical characteristics of liquid crystals, such as transparency, dispersion of light and double refraction, make possible the rendition of numbers, symbols and images.

The possibility of producing opto-electronic components of very low dimensions by utilizing the optical and dielectrical anisotropy of liquid crystals has been in use to a great extent for a long time. Particularly indication systems, which function according to the principle of electro-elastic deformation of twisted homogeneous nematic layers (Schadt-Helfrich-effect), are presently of main interest.

There are always utilized liquid crystal mixtures, because no individual substance can meet the high requirements with respect to mesophase range, chemical stability, viscosity, dielectric and elastic constants, etc. The great interest in the synthesis of new liquid crystalline substances proves that with respect to their various fields of application, the utilized mixtures still remain worthy of improvement.

SUMMARY OF THE INVENTION

The object of the invention is to provide new liquid crystalline substances of broad mesophase ranges which improve the chemical stability of the mixtures.

This and other objects and advantages of the invention will become evident from the description which follows.

It has been found that liquid crystalline 5-alkyl-pyridine-2-carboxylic acid esters of the general formula

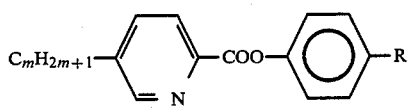

wherein R =

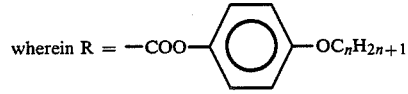

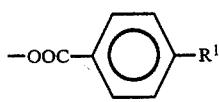

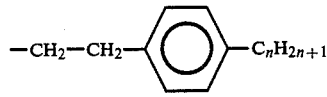

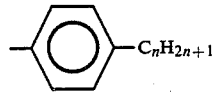

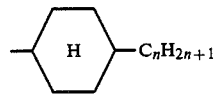

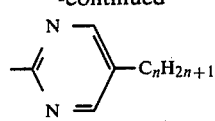

$R^1 = -OC_nH_{2n+1}$, CN, $-C_nH_{2n+1}$ wherein m, n = 1 to 8 are suitable for utilization in electro-optical displays for the rendition of numbers, symbols and images, because they increase the chemical stability of mixtures, which in particular contain hydrolysis-sensitive compounds, for instance, 1,3-dioxane derivatives.

The substances possess broad mesophase ranges, and thus allow to considerably increase the clarification points of mixtures.

DETAILED DESCRIPTION OF THE PREFERRED EMBODIMENTS

The invention will hereafter be more closely explained with examples of the embodiments.

EXAMPLE 1

Production of the 5-n-butyl-pyridine-2-carboxylic acid esters 1.97 g (0.01 mol) of 5-n-butyl-pyridine-2-carboxylic acid chloride dissolved in chloroform are added to the corresponding 4-substituted phenols which are also dissolved in chloroform. The starting reaction substance is heated for 10 minutes in a water bath under exclusion of moisture. Subsequently the solvent is removed at the rotary evaporator and the reaction mixture is heated again to 80° C. The cooled mass is dissolved in ether and the ether solution is washed with a 2.5% $Na_2CO_3$ solution and water. After drying over $Na_2SO_4$ and the removal of the solvent, the residue can be recrystallized out of a little methanol.

Examples for the utilized substances according to the invention which are obtained in this way are given in Tables 1 to 3.

TABLE 1

$C_4H_9$—[pyridine]—COO—[phenyl]—COO—[phenyl]—$OC_nH_{2n+1}$

| No. | n | K | N | I |
|---|---|---|---|---|
| 1/1 | 4 | . 80 | . 174 | . |
| 1/2 | 5 | . 53 | . 140 | . |
| 1/3 | 6 | . 75 | . 171 | . |
| 1/4 | 7 | . 58 | . 156 | . |
| 1/5 | 8 | . 67 | . 161 | . |

TABLE 2

$C_4H_9$—[pyridine]—COO—[phenyl]—OOC—[phenyl]—$R^1$

| No. | $R^1$ | K | N | I |
|---|---|---|---|---|
| 2/1 | $OC_4H_9$ | . 102 | . 176 | . |
| 2/2 | $OC_5H_{11}$ | . 98 | . 175 | . |
| 2/3 | $OC_6H_{13}$ | . 107 | . 187 | . |
| 2/4 | $OC_8H_{17}$ | . 108 | . 177 | . |
| 2/5 | CN | . 165 | . 237 | . |

TABLE 3

C₄H₉—[pyridine]—COO—[phenyl]—R

| No. | R | K | N | I |
|---|---|---|---|---|
| 3/1 | —CH₂—CH₂—[phenyl]—C₄H₉ | . 51 | . 90 | . |
| 3/2 | —[phenyl]—C₂H₅ | . 81 | . 156 | . |
| 3/3 | —[phenyl]—C₆H₁₃ | . 55 | . 140 | . |
| 3/4 | —[pyrimidine]—C₅H₁₁ | . 75 | . 146 | . |

K = crystalline solid
N = nematic
I = isotropic liquid

By means of DSC, the melting enthalpies have been determined for a few substances.

| Substance No. | $\Delta_F H$ kJ/mol |
|---|---|
| 2/4 | 28.7 |
| 3/2 | 19.3 |
| 1/5 | 18.2 |

EXAMPLE 2

For the presentation of the changes of the clarification temperatures, to a mixture 14 of the following composition C₃H₇—[cyclohexyl]—COO—[phenyl]—CN    34.5 mol %

C₄H₉—[cyclohexyl]—COO—[phenyl]—CN    31.0 mol %

C₅H₁₁—[cyclohexyl]—COO—[phenyl]—CN    34.5 mol % substances according to the invention are added.

The clarification temperatures and the electro-optical parameters are summarized in the following chart:

| Mi 14 mol-% | Substance No. | mol-% | Klp. °C. | $U_o$ v | $\tau_E^{50}$ ms | $\tau_A^{50}$ ms |
|---|---|---|---|---|---|---|
| | | | | U = 2 $U_o$ with reference to d = 10 μm | | |
| 100 | — | — | 72 | 1.3 | 101 | 35 |
| 90 | 2/4 | 10 | 88 | 1.7 | 212 | 77 |
| 90 | 3/2 | 10 | 80 | 1.4 | 135 | 11 |
| 90 | 1/5 | 10 | 87 | 1.1 | 251 | 110 | wherein
  Klp = clarification point
  $U_o$ = threshold voltage
  $\tau_E^{50}$ = switching-on period at 50% change of intensity, 20° C., 500 Hz
  $\tau_A^{50}$ = decay period at 50% change of intensity, 20° C., 500 Hz
  d = thickness of layer
  U = operating voltage There have also been performed measurements for the change of the viscosity at addition of substances according to the invention.

| Mixture | η cp |
|---|---|
| 14 | 33.0 |
| 14 + 10% 2/4 | 85.0 |
| 14 + 10% 3/2 | 135.0 |
| 14 + 10% 1/5 | 86.0 |

η = Viscosity at 20° C.

EXAMPLE 3

To a mixture having the composition

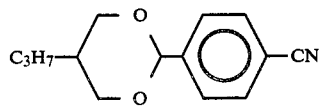

50 mol %  C₃H₇—[dioxane]—[phenyl]—CN

Klp.: 43° C.

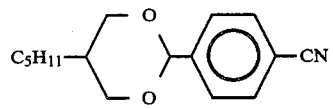

50 mol %  C₅H₁₁—[dioxane]—[phenyl]—CN have been added 20 mol-% of the substances according to the invention. The result was a great increase of the clarification point.

| Added Substance No. | Klp. °C. |
|---|---|
| 1/5 | 69 |
| 2/4 | 70 |
| 3/2 | 68 |

It thus will be seen that there are provided liquid crystalline substances of high chemical stability as additives in nematic mixtures for electro-optical systems which attain the various objects of the invention, and which are well adapted for the conditions of practical use. As numerous alternatives within the scope of the present invention will occur to those skilled in the art, besides those embodiments, equivalents, alternatives and variations mentioned supra, it is to be understood that the invention is to be limited only by the scope of the appended claims, and functional and structural equivalents thereof.

We claim:

1. Liquid crystalline 5-alkyl-pyridine-2-carboxylic acid esters of the general formula

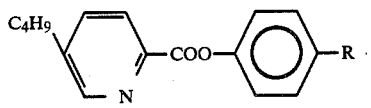

I wherein R =

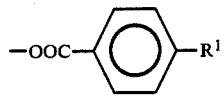

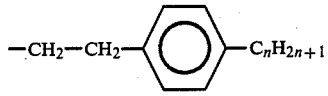

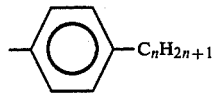

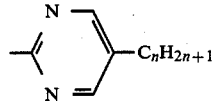

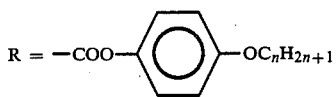

$R^1 = -OC_nH_{2n+1}, CN, -C_nH_{2n+1}$ wherein n = 1 to 8.

2. A liquid crystalline ester according to claim 1, wherein in formula I

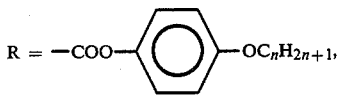

and n=4.

3. A liquid crystalline ester according to claim 1, wherein in formula I

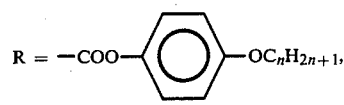

and n=5.

4. A liquid crystalline ester according to claim 1, wherein in formula I

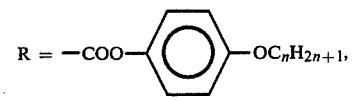

and n=6.

5. A liquid crystalline ester according to claim 1, wherein in formula I

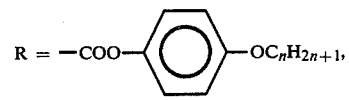

and n=7.

6. A liquid crystalline ester according to claim 1, wherein in formula I

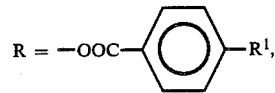

and n=8.

7. A liquid crystalline ester according to claim 1, wherein in formula I

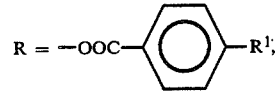

and $R^1 = -OC_4H_9$.

8. A liquid crystalline ester according to claim 1, wherein in formula I

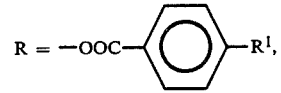

and $R^1 = -OC_5H_{11}$.

9. A liquid crystalline ester according to claim 1, wherein in formula I

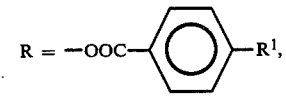

and $R^1 = -OC_6H_{13}$.

10. A liquid crystalline ester according to claim 1, wherein in formula I $R = -OOC$—⟨O⟩—$R^1$, and $R^1 = -OC_8H_{17}$.

11. A liquid crystalline ester according to claim 1, wherein in formula I

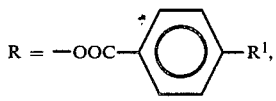

and R¹=CN.

12. A liquid crystalline ester according to claim 1, wherein in formula I

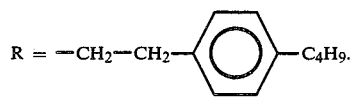

13. A liquid crystalline ester according to claim 1, wherein in formula I

14. A liquid crystalline ester according to claim 1, wherein in formula I

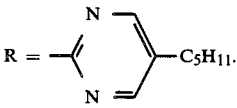

15. A liquid crystalline ester according to claim 1, wherein in formula I $$R = -\left\langle \begin{array}{c} N \\ N \end{array} \right\rangle - C_5H_{11}.$$

16. A mixture comprising an ester according to claim 1 and other liquid crystalline substances.

17. An electro-optical device for the rendition of numbers, symbols or images containing a mixture according to claim 16.

* * * * *